United States Patent [19]
Pikul et al.

[11] Patent Number: 5,830,915
[45] Date of Patent: Nov. 3, 1998

[54] PHOSPHINIC ACID AMIDES AS MATRIX METALLOPROTEASE INHIBITORS

[75] Inventors: Stanislaw Pikul, Mason; Kelly Lynn McDow-Dunham, Loveland; Biswanath De, Cincinnati; Yetunde Olabisi Taiwo, West Chester, all of Ohio

[73] Assignee: The Procter & Gamble Company, Cincinnati, Ohio

[21] Appl. No.: 918,950

[22] Filed: Aug. 26, 1997

Related U.S. Application Data

[60] Provisional application No. 60/024,765 Aug. 28, 1996.
[51] Int. Cl.$^6$ ............ A61K 31/16; A61K 31/38; A61K 31/40; A61K 31/44
[52] U.S. Cl. ............ 514/620; 514/357; 514/396; 514/415; 514/438; 514/451; 514/824; 514/861; 514/863; 514/864; 514/886; 514/902; 514/903; 546/21; 546/336; 546/337; 548/112; 549/6; 549/216
[58] Field of Search ............ 514/357, 396, 514/415, 436, 451, 620, 824, 861, 863, 864, 886, 902, 903; 546/21, 336, 337; 548/112; 549/6, 216; 564/12

[56] References Cited

U.S. PATENT DOCUMENTS

| | | | |
|---|---|---|---|
| 4,918,105 | 4/1990 | Cartwright et al. | 514/575 |
| 4,996,358 | 2/1991 | Handa et al. | 562/621 |
| 5,183,900 | 2/1993 | Galardy et al. | 548/495 |
| 5,189,178 | 2/1993 | Galardy et al. | 548/495 |
| 5,300,674 | 4/1994 | Crimmin et al. | 560/42 |
| 5,310,763 | 5/1994 | Campion et al. | 514/575 |

FOREIGN PATENT DOCUMENTS

| | | | |
|---|---|---|---|
| 0231081 | 8/1987 | European Pat. Off. | C07K 5/06 |
| 0450355 | 10/1991 | European Pat. Off. | A01N 43/10 |
| 0498665 | 2/1992 | European Pat. Off. | C07C 259/06 |
| 0575844 | 12/1993 | European Pat. Off. | C07C 259/06 |
| 0606046 | 7/1994 | European Pat. Off. | C07D 213/42 |
| 4127842 | 2/1993 | Germany | C07D 333/24 |
| 2268934 | 1/1994 | United Kingdom . | |
| WO 91/02716 | 3/1991 | WIPO | C07C 259/06 |
| WO 93/00082 | 6/1992 | WIPO | A61K 31/16 |
| WO 92/17460 | 10/1992 | WIPO | C07C 245/02 |
| WO 93/20047 | 4/1993 | WIPO | C07K 317/44 |
| WO 93/09090 | 5/1993 | WIPO | C07C 259/06 |
| WO 93/21942 | 11/1993 | WIPO | A61K 37/02 |
| WO 94/10990 | 5/1994 | WIPO | A61K 31/16 |
| WO 95/35275 | 12/1995 | WIPO | C07C 311/06 |

OTHER PUBLICATIONS

Chapman, K.T., et al., "Inhibition of Matrix Metalloproteinases by N–Carboxyalkyl Peptides", *Journal of Medicinal Chemistry*, vol. 36 (1993), pp. 4293–4301.

Johnson, w.K., Roberts, N.a., and Borkakoti, N., "Collagenase Inhibitors: Their Design and Potential Therapeutic Use", *Journal of Enzyme Inhibition*, vol. 2 (1987), pp. 1–22.

Schwartz, M.a., Van Wart, H.E., "synthetic Inhibitors of Bacterial and Mammalian Interstitial Collagenases", *Progress in Medicinal chemistry*, vol. 29 (1992), p. 271.

Singh, J., et al. "Relationship Between Structure and Bioavailability in a Series of Hydroxamate Based metalloprotease Inhibitors", *Bioorganic & Medicinal Chemistry Letters*, vol. 5 (1995), pp. 337–342.

Tomczuk, B.E., et al., "Hydroxamate Inhibitors of the Matrix Metallo–Proteinases (MMPs) containing Novel $P_1$ Heteroatom Based Modifications", *bioorganic & Medicinal chemistry Letters*, vol. 5 (1995), pp. 343–348.

Turbanti, L., et al., "1,2–Cyclomethylenecarboxylic Monoamide Hydroxamic Derivatives. A Novel Class of Non–amino Acid Angiotensin Converting Enzyme Inhibitors", *Journal of Medicinal Chemistry*, vol. 36 (1993), pp. 699–707.

*Primary Examiner*—Peter O'Sullivan
*Attorney, Agent, or Firm*—Richard A. Hake; Mary Pat McMahon; David L. Suter

[57] ABSTRACT

The invention provides compounds which are useful as inhibitors of matrix metalloproteases, and which are effective in treating conditions characterized by excess activity of these enzymes. In particular, the present invention relates to a compound having a structure according to Formula (I)

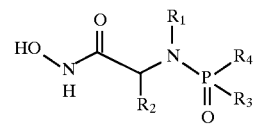

wherein $R_1$, $R_2$, $R_3$ and $R_4$ are described in the claims, a stereoisomer or enantiomer thereof, or a pharmaceutically-acceptable salt, or biohydrolyzable alkoxyamide, ester acyloxyamide, imide or derivative thereof.

Also disclosed are compounds, pharmaceutical compositions and methods of treating diseases characterized by matrix metalloprotease activity using these compounds or the pharmaceutical compositions containing them.

31 Claims, No Drawings

PHOSPHINIC ACID AMIDES AS MATRIX METALLOPROTEASE INHIBITORS

CROSS REFERENCE

This application claims priority under Title 35, United States Code 119(e) from Provisional application Ser. No. 60/024,765, filed Aug. 28, 1996.

TECHNICAL FIELD

This invention is directed to compounds which are useful in treating diseases associated with metalloprotease activity, particularly zinc metalloprotease activity.

BACKGROUND

Background
A number of structurally related metalloproteases [MPs] effect the breakdown of structural proteins. These metalloproteases often act on the intercellular matrix, and thus are involved in tissue breakdown and remodeling. Such proteins are referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane bound metalloproteases, TNF converting enzymes, angiotensin-converting enzymes (ACEs), disintegrins, including ADAMs (See Wolfsberg et al, 131 *J. Cell Bio.* 275–78 October, 1995), and the enkephalinases. Examples of MPs include human skin fibroblast collagenase, human skin fibroblast gelatinase, human sputum collagenase, aggrecanse and gelatinase, and human stromelysin. Collagenase, stromelysin, aggrecanase and related enzymes are thought to be important in mediating the symptomatology of a number of diseases.

Potential therapeutic indications of MP inhibitors have been discussed in the literature. See for example, U.S. Pat. No. 5,506,242 (Ciba Geigy Corp.); U.S. Pat. No. 5,403,952 (Merck & Co.); PCT 30 published application WO 96/06074 (British Bio Tech Ltd); PCT Publication WO 96/00214 (Ciba Geigy); WO 95/35275 (British Bio Tech Ltd); WO 95/35276 (British Bio Tech Ltd); WO 95/33731 (Hoffman-LaRoche); WO 95/33709 (Hoffman-LaRoche); WO 95/32944 (British Bio Tech Ltd);

WO 95/26989 (Merck); WO 9529892 (DuPont Merck); WO 95/24921 (Inst. Opthamology); WO 95/23790 (SmithKline Beecham); WO 95/22966 (Sanofi Winthrop); WO 95/19965 (Glycomed); WO 95 19956 (British Bio Tech Ltd); WO 95/19957 (British Bio Tech Ltd); WO 95/19961 (British Bio Tech Ltd) WO 95/13289 (Chiroscience Ltd.); WO 95/12603 (Syntex); WO 95/09633 (Florida State Univ); WO 95/09620 (Florida State Univ.); WO 95/04033 (Celltech); WO 94/25434 (Celltech); WO 94/25435 (Celltech); WO 93/14112 (Merck); WO 94/0019 (Glaxo); WO 93/21942 (British Bio Tech Ltd); WO 92/22523 (Res. Corp. Tech. Inc.); WO 94/10990 (British Bio Tech Ltd); WO 93/09090 (Yamanouchi); and British patents GB 2282598 (Merck) and GB 2268934 (British Bio Tech Ltd); Published European Patent Applications EP 95/684240 (Hoffman LaRoche); EP 574758 (Hoffman LaRoche); EP 575844 (Hoffman LaRoche); Published Japanese applications; JP 08053403 (Fujusowa Pharm. Co. Ltd.); JP 7304770 (Kanebo Ltd.); and Bird et al *J. Med Chem* vol. 37, pp. 158–69 (1994). Examples of potential therapeutic uses of MP inhibitors include rheumatoid arthritis (Mullins, D. E., et al., *Biochim. Biophys. Acta.* (1983) 695: 117–214); osteoarthritis (Henderson, B., et al., *Drugs of the Future* (1990) 15: 495–508); the metastasis of tumor cells (ibid, Broadhurst, M. J., et al., European Patent Application 276,436 (published 1987), Reich, R., et al., 48 *Cancer Res.* 3307–3312 (1988); and various ulcerations or ulcerative conditions of tissue. For example, ulcerative conditions can result in the cornea as the result of alkali burns or as a result of infection by *Pseudomonas aeruginosa*, Acanthamoeba, Herpes simplex and vaccinia viruses.

Other examples of conditions characterized by undesired metalloprotease activity include periodontal disease, epidermolysis bullosa, fever, inflammation and scleritis (Cf. DeCicco et al, WO 95 29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13, 1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication Number 498,665, published Aug. 12, 1992 by Beckett, et al.

Though a variety of inhibitors have been prepared, there is a continuing need for potent matrix metalloprotease inhibitors useful in treating such diseases. It would be advantageous to inhibit these metalloproteases as a method of treating diseases related to unwanted metalloprotease activity. Though a variety of inhibitors have been prepared, there is a continuing need for potent metalloprotease inhibitors useful in treating such diseases.

OBJECTS OF THE INVENTION

It is an object of the invention to provide potent inhibitors of metalloproteases.

It is a further object of the invention to provide pharmaceutical compositions comprising such inhibitors.

It is also an object of the invention to provide a method of treatment for metalloprotease related maladies.

SUMMARY OF THE INVENTION

The invention provides compounds which are useful as inhibitors of matrix metalloproteases, and which are effective in treating conditions characterized by excess activity of these enzymes. In particular, the present invention relates to a compound having a structure according to Formula (I)

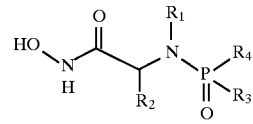

wherein:
  $R_1$ is hydrogen, alkyl, aryl-alkyl, heterocycle-alkyl, alkoxy-alkyl, arylalkoxy-alkyl, or alkylthioalkyl;
  $R_2$ is hydrogen, alkyl, aryl-alkyl, heterocycle-alkyl, alkoxy-alkyl, arylalkoxy-alkyl, or alkylthioalkyl;
  $R_3$ is alkyl, cycloalkyl, carbocyclic or heterocyclic aryl, hydroxyalkyl, alkoxyalkyl, or aminoalkyl; and
  $R_4$ is carbocyclic or heterocyclic aryl;

an optical isomer, diastereomer or enantiomer thereof, or a pharmaceutically-acceptable salt, or biohydrolyzable alkoxyamide, ester acyloxyamide, or imide thereof.

Preferred $R_4$ include phenyl and substituted phenyl. Preferred substitution on $R_4$ is adjacent to the attachment or opposite to it (i.e., if $R_4$ is phenyl, then at the 2 and/or 4 positions). Preferred phenyl substituents include halo, alkyl, alkoxy, nitro, cyano and the like. Preferred $R_3$ are alkyl, more preferably $C_1$–$C_2$ alkyl. Preferred $R_2$ are H or alkyl, more preferably H or $C_1$–$C_4$ alyl. Preferred $R_1$ are H or alkyl, arylalkyl, more preferably $C_1$–$C_6$ alkyl or aryl ($C_1$–$C_2$) alkyl.

These compounds have the ability to inhibit at least one mammalian matrix metalloprotease. Accordingly, in other aspects, the invention is directed to pharmaceutical compositions containing the compounds of Formula (I), and to methods of treating diseases characterized by matrix metalloprotease activity using these compounds or the pharmaceutical compositions containing them.

Matrix metalloproteases active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired matrix metalloprotease.

In another aspect, the invention is directed to the compounds of Formula (I) conjugated to label. As the compounds of the invention bind to at least one matrix metalloprotease, the label can be used to detect the presence of relatively high levels of matrix metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

DETAILED DESCRIPTION

The compounds of the present invention are inhibitors of mammalian matrix metalloproteases. Preferably, the compounds are those of Formula (I) or a pharmaceutically-acceptable salt, or biohydrolyzable alkoxyamide, acyloxyamide, or imide thereof.

Definitions and Usage of Terms:

The following is a list of definitions for terms used herein.

"Acyl" or "carbonyl" is described as a radical which could be formed by removal of the hydroxy from a carboxylic acid (i.e., R—C(=O)—). Preferred acyl groups include (for example) acetyl, formyl, and propionyl.

"Acyloxy" is an oxy radical having an acyl substituent (i.e., —O-acyl); for example, —O—C(=O)-alkyl.

"Alkoxyacyl" is an acyl radical (—C(=O)—) having an alkoxy substituent (i.e., —O—R), for example, —C(=O)—O-alkyl. This radical can be referred to as an ester.

"Acylamino" is an amino radical having an acyl substituent (i.e., —N-acyl); for example, —NH—C(=O)-alkyl.

"Alkenyl" is an unsubstituted or substituted hydrocarbon chain radical having 2 to 15 carbon atoms; preferably from 2 to 10 carbon atoms; more preferably from 2 to 8; except where indicated. Alkenyl substituents have at least one olefinic double bond (including, for example, vinyl, allyl and butenyl).

"Alkynyl" is an unsubstituted or substituted hydrocarbon chain radical having 2 to 15 carbon atoms; preferably from 2 to 10 carbon atoms; more preferably from 2 to 8; except where indicated. The chain has at least one carbon-carbon triple bond.

"Alkoxy" is an oxygen radical having a hydrocarbon chain substituent, where the hydrocarbon chain is an alkyl or alkenyl (i.e., —O-alkyl or —O-alkenyl). Preferred alkoxy groups include (for example) methoxy, ethoxy, propoxy and allyloxy.

"Alkoxyalkyl" is an unsubstituted or substituted alkyl moiety substituted with an alkoxy moiety (i.e., —alkyl-O-alkyl). Preferred is where the alkyl has 1 to 6 carbon atoms (more preferably 1 to 3 carbon atoms), and the alkyoxy has 1 to 6 carbon atoms (more preferably 1 to 3 carbon atoms).

"Alkyl" is an unsubstituted or substituted saturated hydrocarbon chain radical having 1 to 15 carbon atoms; preferably from 1 to 10 carbon atoms; more preferably 1 to 4; except where indicated. Preferred alkyl groups include (for example) substituted or unsubstituted methyl, ethyl, propyl, isopropyl, and butyl.

As referred to herein, "spiro cycle" or "spiro cyclic" refers to a cyclic moiety sharing a carbon on another ring. Such cyclic moiety may be carbocyclic or heterocyclic in nature. Preferred heteroatoms included in the backbone of the heterocyclic spirocycle include oxygen, nitrogen and sulfur. The spiro cycles may be unsubstituted or substituted. Preferred substituents include oxo, hydroxy, alkyl, cycloalkyl, arylalkyl, alkoxy, amino, heteroalkyl, aryloxy, fused rings (e.g., benzothiole, cycloalkyl, heterocycloalkyl, benzimidizoles, pyridylthiole, etc., which may also be substituted) and the like. In addition, the heteroatom of the heterocycle may be substituted if valence allows. Preferred spirocyclic ring sizes include 3–7 membered rings.

Alkylene refers to an alkyl, alkenyl or alkynyl which is diradical, rather than a radical. "Hetero alkylene" is likewise defined as a (diradical) alkylene having a heteroatom in its chain.

"Alkylamino" is an amino radical having one (secondary amine) or two (tertiary amine) alkyl substituents (i.e., —N-alkyl). For example, methylamino (—NHCH$_3$), dimethylamino (—N(CH$_3$)$_2$), methylethylamino (—N(CH$_3$)CH$_2$CH$_3$).

"Aminoacyl" is acyl radical having an amino substituent (i.e., —C(=O)—N); for example, —C(=O)—NH$_2$. The amino group of the aminoacyl moiety may be unsubstituted (i.e., primary amine) or may be substituted with one (secondary amine) or two (i.e., tertiary amine) alkyl groups.

"Aryl" is an aromatic carbocyclic ring radical. Preferred aryl groups include (for example) phenyl, tolyl, xylyl, cumenyl, naphthyl, biphenyl and fluorenyl. Such groups may be substituted or unsubstituted.

"Arylalkyl" is an alkyl radical substituted with an aryl group. Preferred arylalkyl groups include benzyl, phenylethyl, and phenylpropyl. Such groups may be substituted or unsubstituted. "Arylalkylamino" is an amine radical substituted with an arylalkyl group (e.g., —NH-benzyl). Such groups may be substituted or unsubstituted.

"Arylamino" is an amine radical substituted with an aryl group (i.e., —NH-aryl). Such groups may be substituted or unsubstituted.

"Aryloxy" is an oxygen radical having an aryl substituent (i.e., —O-aryl). Such groups may be substituted or unsubstituted.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain 4 to 9 atoms, preferably 4 to 7 atoms. Polycyclic carbocyclic rings contain 7 to 17 atoms, preferably from 7 to 12 atoms. Preferred polycyclic systems comprise 4-, 5-, 6- or 7-membered rings fused to 5-, 6-, or 7-membered rings.

"Carbocycle-alkyl" is an unsubstituted or substituted alkyl radical substituted with a carbocyclic ring. Unless otherwise specified, the carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. Unless otherwise specified, the carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carboxyalkyl" is an unsubstituted or substituted alkyl radical substituted with a carboxy (—C(=O)OH) moiety. For example, —CH$_2$—C(=O)OH.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholinyl, piperadinyl, piperazinyl, tetrahydrofuryl and hydantoinyl.

"Fused rings" are rings that are superimposed together such that they share two ring atoms. A given ring may be fused to more than one other ring. Fused rings are contemplated in heteroaryl, aryl and heterocycle radicals or the like.

"Heterocycle-alkyl" is an alkyl radical substituted with a heterocyclic ring. The heterocyclic ring is preferably a heteroaryl or cycloheteroalkyl; more preferably a heteroaryl. Preferred heterocycle alkyl include $C_1$–$C_4$ alkyl having preferred heteroaryl appended to them. More preferred is, for example, pyridyl alkyl, and the like.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkenyl" is an unsubstituted or substituted unsaturated chain radical having 3 to 8 members comprising carbon atoms and one or two heteroatoms. The chain has at least one carbon-carbon double bond.

"Heteroalkyl" is an unsubstituted or substituted saturated chain radical having 2 to 8 members comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain 3 to 9 atoms, preferably 4 to 7 atoms. Polycyclic rings contain 7 to 17 atoms, preferably from 7 to 13 atoms.

"Heteroaryl" is an aromatic heterocyclic ring, either monocyclic or bicyclic radical. Preferred heteroaryl groups include (for example) thienyl, furyl, pyrrolyl, pyridinyl, pyrazinyl, thiazolyl, pyrimidinyl, quinolinyl, and tetrazolyl, benzo thiazolyl, benzofuryl, indolyl and the like. Such groups may be substituted or unsubstituted.

"Halo", "halogen", or "halide" is a chloro, bromo, fluoro or iodo atom radical. Bromo, chloro and fluoro are preferred halides.

Also, as referred to herein, a "lower" hydrocarbon moiety (e.g., "lower" alkyl) is a hydrocarbon chain comprised of 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium) and organic salts. Preferred anionic salts include the halides (such as chloride salts).

"Biohydrolyzable alkoxyamide" and "Biohydrolyzable acyloxyamide" are amides of a hydroxamic acid that do not essentially interfere with the inhibitory activity of the compound, or that are readily converted in vivo by a human or lower animal subject to yield an active hydroxamic acid.

A "biohydrolyzable hydroxy imide" is an imide of a Formula (I) compound that does not interfere with the metalloprotease inhibitory activity of these compounds, or that is readily converted in vivo by a human or lower animal subject to yield an active Formula (I) compound. Such hydroxy imides include those that do not interfere with the biological activity of the Formula (I) compounds.

A "biohydrolyzable ester" refers to an ester of a Formula (I) compound that does not interfere with the metalloprotease inhibitory activity of these compounds or that is readily converted by an animal to yield an active Formula (I) compound.

A "solvate" is a complex formed by the combination of a solute (e.g., a hydroxamic acid) and a solvent (e.g., water). See J. Honig et al., *The Van Nostrand Chemist's Dictionary*, p. 650 (1953). Pharmaceutically-acceptable solvents used according to this invention include those that do not interfere with the biological activity of the hydroxamic acid (e.g., water, ethanol, acetic acid, N,N-dimethylformamide and others known or readily determined by the skilled artisan).

"Optical isomer", "stereoisomer", "diastereomer" as referred to herein have the standard art recognized meanings (Cf., *Hawleys Condensed Chemical Dictionary*, 11th Ed.).

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein, "mammalian matrix metalloprotease" means any metal-containing enzyme found in mammalian sources which is capable of catalyzing the breakdown of collagen, gelatin or proteoglycan under suitable assay conditions. Appropriate assay conditions can be found, for example, in U.S. Pat. No. 4,743,587, which references the procedure of Cawston, et al., Anal Biochem (1979) 99: 340–345, use of a synthetic substrate is described by Weingarten, H., et al., Biochem Biophy Res Comm (1984) 139: 1184–1187. Any standard method for analyzing the breakdown of these structural proteins can, of course, be used. The matrix metalloprotease enzymes referred to herein are all zinc-containing proteases which are similar in structure to, for example, human stromelysin or skin fibroblast collagenase. The ability of candidate compounds to inhibit matrix metalloprotease activity can, of course, be tested in the assays described above. Isolated matrix metalloprotease enzymes can be used to confirm the inhibiting activity of the invention compounds, or crude extracts which contain the range of enzymes capable of tissue breakdown can be used.

Compounds:

Compounds of the invention are described in the Summary of the Invention. Preferred compounds of Formula (I) include

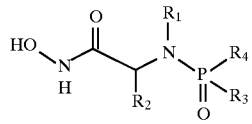

wherein:

$R_1$ is hydrogen, alkyl, aryl-alkyl, heterocycle-alkyl, alkoxy-alkyl, arylalkoxy-alkyl, or alkylthioalkyl;

$R_2$ is hydrogen, alkyl, aryl-alkyl, heterocycle-alkyl, alkoxy-alkyl, arylalkoxy-alkyl, or alkylthioalkyl;

$R_3$ is alkyl, cycloalkyl, carbocyclic or heterocyclic aryl, hydroxyalkyl, alkoxyalkyl, or aminoalkyl; and $R_4$ is carbocyclic or heterocyclic aryl;

an optical isomer, diastereomer or enantiomer thereof, or a pharmaceutically-acceptable salt, or biohydrolyzable alkoxyamide, ester acyloxyamide, or imide thereof.

Compound Preparation:

The hydroxamic compounds of Formula (I) can be prepared using a variety of procedures. General schemes include the following. (Representative examples are described for making specific compounds hereinbelow);

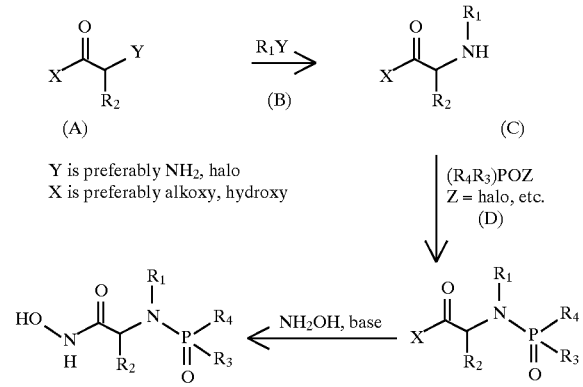

The compounds of Formula (I) are easily prepared from compounds of formula (A) $R_2$ amino acids, $R_2$ 2-halo esters and the like. For compound A, Y is preferably amino and is reacted with compound B when Y is halo or a suitable leaving group. For compound A, with Y as halo, the skilled artisan will immediately recognize that compound B has Y as amino. Where $R_1$ and $R_2$ do not form a single chain, the $R_1$ moiety (B) is introduced using conventional methods. For example, where a 2-halo ester is used, an $R_1$ primary amino compound under basic conditions displaces the halide or if an amino acid is used it can be treated with an $R_1$ carbonyl compound such as an aldehyde and then the oxy moiety can be reduced by conventional means to produce C. When the compounds of formula A can be derived from known amino acids, including the 20 commonly occurring <amino acids, their derivatives (e.g., sarcosine hydroxy proline 2-amino butyric acid, pipicolic acid and the like), or any such d amino acids. Many are know or commercially available, such as from Sigma (St. Louis, Mo.) or Aldrich (Milwaukee, Wis.). For those that are not easily available, $R_2$ amino acid variants can be made by any of several methods known in the art.

Where it is more advantageous to make compounds of Formula I using a halo ester or halo acid, such halo esters and halo acids are known in the art, or made by well known methods (see for example March, Advanced Organic Chemistry, Wiley Interscience.

The $R_3R_4POZ$ compound is made using standard methodologies. For example, $PCl_3$ may be alkylated and/or arylated to form $RPCl_2$ or $R_3RPCl$ then treated with a short chain alkanol to form $R_3R_4POZ$.

Alternatively, where $R_3$ and $R_1$ form a ring, the XC(O) $CHR_2NH_2$ compound can be reacted under standard condition to form $XC(O)CHR_2NA(R_1R_3)POCl$ which then closes to form.

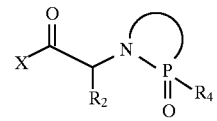

Preferably $(R_1R)$ is oxymethyene or oxyethylene.

Where $R_4$ is heterocyclic, methods for making the phosphinyl or phosponyl derivatives thereof are known in the art. Preferred heterocyclic $R_4$ radicals include 2 or 3 thienyl, 2 or 3 furyl, 2, 3, or 4 pyridyl, pyrmidyl and the like.

The $(R_3R_4)$ PO moiety (D) is introduced using standard phosphonamide chemistry such as treatment of the amine with a phosphoryl chloride in an inert solvent and the like.

Typically the hydroxamic acid is elaborated in a final step by treatment with hydroxyl amine using known methodology.

These steps may be varied to increase yield of desired product. The skilled artisan will also recognize the judicious choice of reactants, solvents, and temperatures is an important component in successful synthesis. While the determination of optimal conditions, etc. is routine, it will be understood that to make a variety of compounds can be generated in a similar fashion, using the guidance of the scheme above.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations, acylations, aromatic substitutions, both electrophilic and nucleophilic, etherifications, esterification and soponification and the like. Examples of these manipulations are discussed in standard texts such as March, Advanced Organic Chemistry (Wiley), Carey and Sundberg, Advanced Organic Chemistry (Vol. 2) and Keeting, Heterocyclic Chemistry (all 17 volumes).

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Methods of use

Metalloproteases (MPs) found in the body operate, in part, by breaking down the extracellular matrix, which comprises extracellular proteins and glycoproteins. These proteins and glycoproteins play an important role in maintaining the size, shape, structure and stability of tissue in the body. Inhibitors of metalloproteases are useful in treating diseases caused, at least in part, by breakdown of such proteins. It is known that MPs are intimately involved in tissue remodeling. As a result of this activity they have been said to be active in many disorders involving either the:

breakdown of tissues; including degenerative diseases, such as arthritis, multiple sclerosis and the like; metastasis or mobility of tissues in the body:

the remodeling of tissues, including fibrotic disease, scarring, benign hyperplasia, and the like.

The compounds of the present invention treat disorders, diseases and/or unwanted conditions which are characterized by unwanted or elevated activity by that class of proteases. For example the compounds can be used to inhibit proteases which destroy structural proteins (i.e. the proteins that maintain tissue stability and structure);

interfere in inter/intracellular signaling, including those implicated in cytokine up-regulation, and/or cytokine processing and/or inflammation, tissue degradation and other maladies [Mohler K. M., et al, Nature 370 (1994) 218–220, Gearing A. J. H., et al, Nature 370 (1994) 555–557 McGeehan G. M., et al, Nature 370 (1994) 558–561], and/or facilitate processes which are undesired in the subject being treated, for example, the processes of sperm maturation, egg fertilization and the like.

As used herein, a "MP related disorder" or "a MP related disease" is one that involves unwanted or elevated MP activity in the biological manifestation of the disease or disorder; in the biological cascade leading to the disorder; or as a symptom of the disorder. This "involvement" of the MP includes;

The unwanted or elevated MN activity as a "cause" of the disorder or biological manifestation, whether the activity was elevated genetically, by infection, by autoimiunity, trauma, biomechanical causes, lifestyle [e.g. obesity] or by some other cause;

The MP as part of the observable manifestation of the disease or disorder. That is, the disease or disorder is measurable in terms of the increased MN activity, or from a clinical standpoint, unwanted or elevated MP levels indicate the disease. MPs need not be the "hallmark" of the disease or disorder;

The unwanted or elevated MP activity is part of the biochemical or cellular cascade that results or relates to the disease or disorder. In this respect, inhibition of the MP activity interrupts the cascade, and thus controls the disease.

Advantageously, many MPs are not distributed evenly throughout the body. Thus the distribution of MPs expressed in various tissues are often specific to those tissues. For example, the distribution of metalloproteases implicated in the breakdown of tissues in the joints, is not the same as the distribution of metalloproteases found in other tissues. Thus, though not essential for activity or efficacy, certain disorders preferably are treated with compounds that act on specific MPs found in the affected tissues or regions of the body. For example, a compound which displays a higher degree of affinity and inhibition for a MP found in the joints (e.g. chondrocytes) would be preferred for treatment of disease found there than other compounds which are less specific.

In addition, certain inhibitors are more bioavialable to certain tissues than others, and this judicious choice of inhibitor, with the selectivity described above provides for specific treatment of the disorder, disease or unwanted condition. For example, compounds of this invention vary in their ability to penetrate into the central nervous system. Thus compounds may be selected to produce effects mediated through MPs found specifically outside the central nervous system.

Determination of the specificity of a MP inhibitor of a certain MP is within the skill of the artisan in that field. Appropriate assay conditions can be found in the literature. Specifically assays are known for stromelysin and collagenase. For example, U.S. Pat. No. 4,743,587 references the procedure of Cawston, et al., *Anal Biochem* (1979) 99: 340–345. The use of a synthetic substrate in an assay is described by Weingarten, H., et al., *Biochem Biophy Res Comm* (1984) 139: 1184–1187. Any standard method for analyzing the breakdown of structural proteins by MPs can, of course, be used. The ability of compounds of the invention to inhibit metalloprotease activity can, of course, be tested in the assays found in the literature, or variations thereof Isolated metalloprotease enzymes can be used to confirm the inhibiting activity of the invention compounds, or crude extracts which contain the range of enzymes capable of tissue breakdown can be used.

As a result of the MP inhibitory effect of the compounds of the invention, the compounds of he invention are also useful in treating the following disorders by virtue of their metalloprotease activity.

The compounds of this invention are also useful for the prophylactic or acute treatment. They are administered in any way the skilled artisan in the fields of medicine or pharmacology would desire. It is immediately apparent to the skilled artisan that preferred routes of administration will depend upon the disease state being treated, and the dosage form chosen. Preferred routes for systemic administration include administration perorally or parenterally.

However, the skilled artisan will readily appreciate the advantage of administering the MP inhibitor directly to the affected area for many disorders. For example, it may be advantageous to administer MP inhibitors directly to the area of the disease or condition as in area affected by surgical trauma (e.g., angioplasty), area affected by scarring or burn (e.g., topical to the skin).

Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive puimonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultaviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus; [CMV] retinitis: HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response, and in the processing of cytokines the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid arthritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erythmatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumitoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis).

Compounds preferred for, but not limited to, the treatment of arthritis (including osteoarthritis and rheumatoid arthritis) are those compounds that are selective for the matrix metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

Compositions:

The compositions of the invention comprise:
(a) a safe and effective amount of a compound of Formula (I); and
(b) a pharmaceutically-acceptable carrier.

As discussed above, numerous diseases are known to be mediated by excess or undesired matrix-destroying metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit matrix metalloproteases at the site(s) of activity, in a human or lower animal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to a human or lower animal subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharmaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tweens®; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

Various oral dosage forms can be used, including such solid forms as tablets, capsules, granules and bulk powders. These oral forms comprise a safe and effective amount, usually at least about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel® RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emolients, emulsifiers, thickening agents, solvents and the like.

Methods of Administration:

This invention also provides methods of treating or preventing disorders associated with excess or undesired matrix metalloprotease activity in a human or other animal subject, by administering a safe and effective amount of a Formula (I) compound to said subject. As used herein, a "disorder associated with excess or undesired matrix metalloprotease activity" is any disorder characterized by degradation of matrix proteins. The methods of the invention are useful in treating disorders such as (for example) osteoarthritis, periodontitis, corneal ulceration, tumor invasion, and rheumatoid arthritis.

The Formula (I) compounds and compositions of this invention can be administered topically or systemically. Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, are mutually dependent. The dosage and treatment regimen will also depend upon such factors as the specific Formula (I) compound used, the treatment indication, the ability of the Formula (I) compound to reach minimum inhibitory concentrations at the site of the matrix metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 300 mg, of Formula (I) compound are administered per day. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the matrix metalloprotease is accumulated by using targeting ligands. For example, to focus the inhibitors to matrix metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases although generally at a lower level than that exhibited with respect to mammalian metalloproteases. Some bacterial metalloproteases seem to be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies:

The invention compounds can also be utilized in immunization protocols to obtain antisera immunospecific for the invention compounds. As the invention compounds are relatively small, they are advantageously coupled to antigenically neutral carriers such as the conventionally used keyhole limpet hemocyanin (KLH) or serum albumin carriers. For those invention compounds having a carboxyl functionality, coupling to carrier can be done by methods generally known in the art. For example, the carboxyl residue can be reduced to an aldehyde and coupled to carrier through reaction with sidechain amino groups in protein-based carriers, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifanctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetitm 99 or I-131, using standard coupling methods. The labeled compounds are administered to subjects to determine the locations of excess amounts of one or more matrix metalloproteases in vivo. The ability of the inhibitors to selectively bind matrix metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

Compound Preparations

Compounds are prepared as represented by the synthetic scheme below.

EXAMPLE I

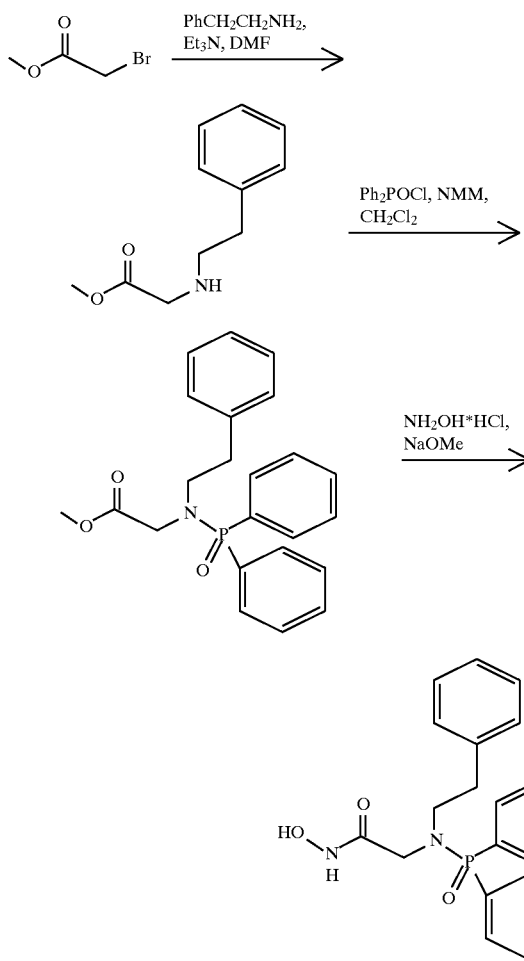

N-(2-Phenethyl)glycine methyl ester: A solution of phenylethylalanine (6.63 mL, 52.8 mmol) and triethylamine (7.39 mL, 53 mmol) in anhydrous N,N-dimethylformamide (80 mL) is cooled to 0° C. and to this mixture is dropwise added a solution of methylbromoacetate (5 mL, 52.8 mmol) in anhydrous N,N-dimethylformamide (40 mL). The reaction is allowed to stir 20 minutes at 0° C. The mixture is poured into 250 mL of ethyl acetate and washed with water (3×), dried over sodium sulfate, and evaporated to give a colorless oil. The hydrochloride is prepared by dissolving the crude oil in 75 mL ether. Aside, 3.8 mL acetyl chloride is added dropwise to 2.5 mL methanol at 0° C. This solution is added dropwise to the ether solution. The precipitated solids are collected by filtration to give 9.2 g (76%) of N-(2-phenethyl) glycine methyl ester hydrochloride as a colorless solid.

N-(Diphenylphosphinyl)-N-(2-phenylethyl)glycine methyl ester: Diphenylphosphinic chloride (0.42 mL, 2.2 mmol) is dissolved in dichloromethane (5 mL) and cooled to 0° C. To this is added a solution of N-(2-phenethyl)glycine methyl ester (500 mg, 2.2 mmol) and N-methylmorpholine (0.73 mL, 6.6 mmol) in dichloromethane (5 mL). The reaction is stirred for 16 hours at room temperature, washed with water and brine, dried over sodium sulfate, and concentrated to give N-(diphenylphosphinyl)-N-(2-phenylethyl)glycine methyl ester as a colorless solid.

N-Hydroxy-2-[[diphenylphosphinyl](2-phenylethyl)-amino]-acetamide: N-(Diphenyl phosphinyl)-N-(2-phenylethyl)glycine methyl ester (160 mg, 0.41 mmol) is dissolved in methanol (2.5 mL). To this is added hydroxylamine hydrochloride (57 mg, 0.81 mmol), followed by a 2 mmol of a 25% methanolic solution of sodium methoxide. The reaction is stirred for 16 hours, neutralized with 1N hydrochloric acid and concentrated. The crude product is purified by silica gel flash chromatography to give 41.6 mg (26%) of N-hydroxy-2-[[diphenylphosphinyl](2-phenylethyl)-amino]-acetamide as a colorless solid: MS-IS m/z 395 [M+H]$^+$, 417 [M+Na]$^+$, 433 [M+K]$^+$. ($R_1$=phenyl ethyl, $R_2$=H, $R_3$=phenyl, $R_4$=phenyl).

EXAMPLE 2

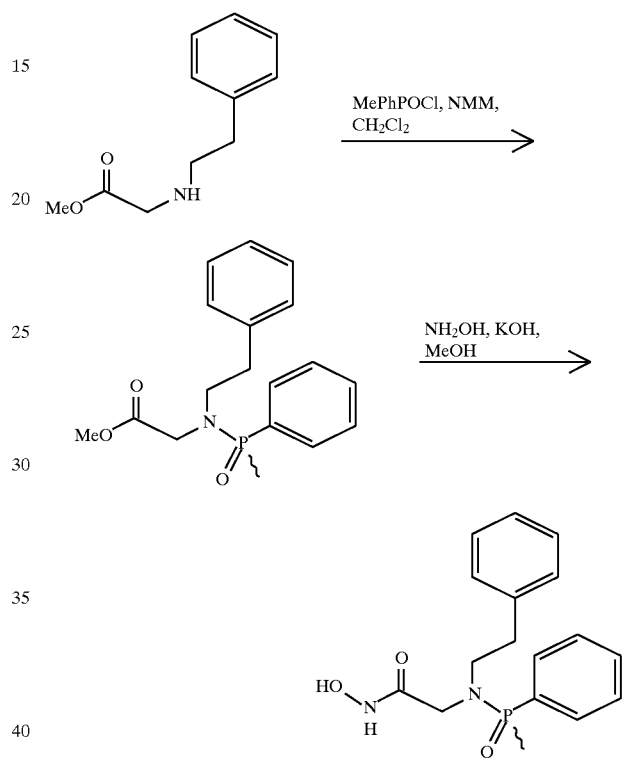

N-Methylphenylphosphinyl)-N-(2-phenylethyl)glycine methyl ester: Methylphenyl-phosphinic chloride (0.45 mL, 3.26 mmol) is dissolved in dichloromethane (5mL) and then cooled to 0° C. To this is added dropwise a solution of 750 mg (3.27 mmol) of N-(2-phenethyl)glycine methyl ester and N-methylmorpholine (1.1 mL, 10 mmol), in dichloromethane (5 mL). The reaction mixture is stirred for 1 hour, warming to room temperature. The mixture is diluted with ethyl acetate, the organic phase is washed with water then brine, and dried over anhydrous sodium sulphate. The crude product is purified by silica gel flush chromatography to give N-(methylphenylphosphinyl)-N-(2-phenylethyl) glycine methyl ester as a colorless oil.

N-Hydroxy-2-[[methylphenylphosphinyl](2-phenylethyl)-amino]-acetamide: N-(Methylphenylphosphinyl)-N-(2-phenylethyl)glycine methyl ester (300 mg, 0.905 mmol) is treated with 0.77 mL of $NH_2OK$ (1.76M in methanol, solution prepared as described in Fieser and Fieser, Vol. 1, p. 478). The mixture is stirred for 3 hours at room temperature, neutralized with formic acid and concentrated. The crude product is purified by silica gel flash chromatography (85:15 ethyl acetate:ethanol) giving the product with slight impurities. Preparative TLC (90:10 ethyl acetate:ethanol) gives N-hydroxy-2-[[methyl phenylphosphinyl](2-phenylethyl)-amino]-acetamide as a colorless solid: MS-IS m/z 333 [M+H]+, 350 [M+NH4]+, 355 [M+Na]+, 371 [M+K]+. (R1=phenyl ethyl, R2=H, R3=methyl, R4=phenyl).

EXAMPLE 3

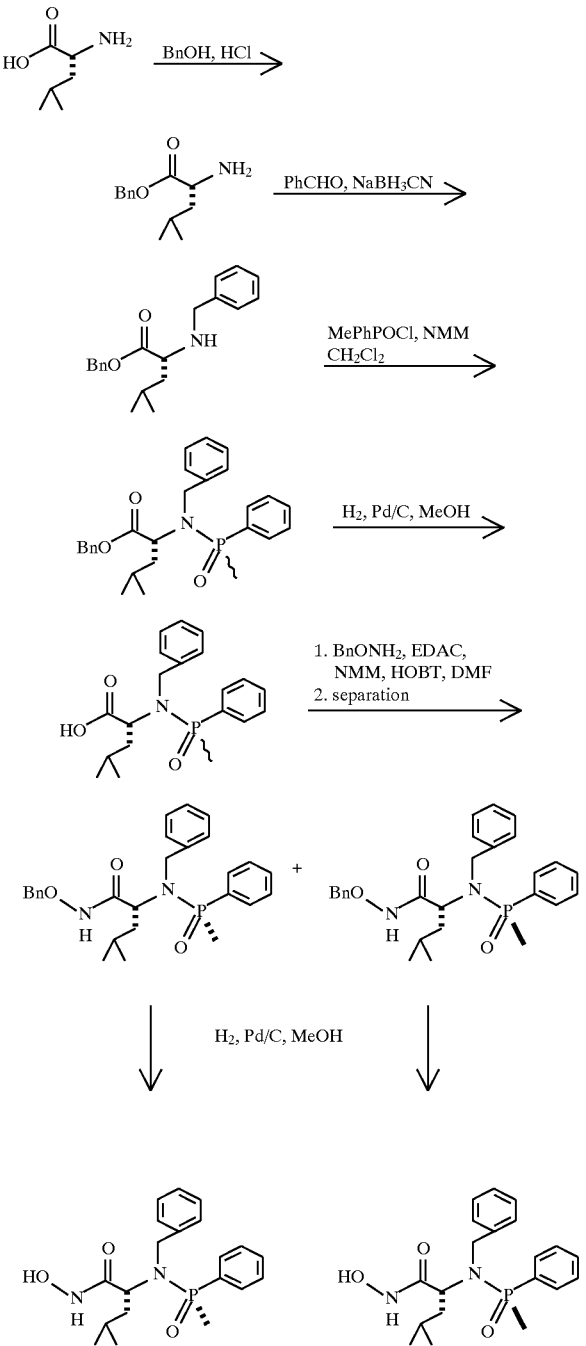

D-Leucine benzyl ester: D-leucine (10 g, 76.23 mmol) is suspended in benzyl alcohol (157 mL) and warmed to 55° C. HCl gas is bubbled through the mixture and the reaction becomes quite viscous. 150 mL of benzene is then added with vigorous stirring. After 30 minutes of bubbling gas through with heating the mixture begins to thin and stirring is achieved more easily. The reaction stirs further at 55° C. for one hour until the solution becomes homogeneous. Flow of HCl is ceased and the reaction is closed off and allowed to stir further at 55° C. for 30 minutes. The reaction is allowed to cool to room temperature and is diluted with ethyl acetate. The product is extracted into 1M HCl (3×) and the organics are discarded. The aqueous washings are combined taken to pH 8 with 50% aqueous NaOH. The amine is extracted several times with ethyl acetate. The organics are dried over sodium sulfate and evaporated. Ether is added to the oil and HCl is bubbled through to precipitate D-leucine benzyl ester as the hydrochloride salt.

N-Benzyl D-leucine benzyl ester: D-Leucine methyl ester (3 g, 11.66 mmol) is dissolved in methanol and to this is added sodium acetate (1.9 g, 23.3 mmol) followed by benzaldehyde (1.2 mL, 11.66 mmol). The mixture is allowed to stir 10 minutes followed by the dropwise addition of a solution of sodium cyanoborohydride (427 mg, 6.8 mmol) in methanol (4 mL). The reaction stirs 3 hours at which time is determined complete by TLC. To the reaction is added 10% aqueous $NaHCO_3$ with stirring. The volatile are then reduced and the product is extracted into ether (3×). The organics are washed with water (2×), dried over sodium sulfate, and evaporated to give N-benzyl D-leucine benzyl ester as a colorless oil.

N-(R/S-Methylphenylphosphinyl)-N-benzyl-D-leucine benzyl ester: Methyl phenyl phosphinic chloride (0.89 mL, 6.42 mmol) is dissolved in dichloromethane and cooled to 0° C. To this is added a solution of N-benzyl D-leucine methyl ester (2g, 6.42 mmol), and N-methyl morpholine (1.5 mL, 13.48 mmol) in dichloromethane. A catalytic amount of 4-dimethylaminopyridine is added and the reaction is allowed to stir for 22 hours. The reaction mixture is concentrated and to the residue is added ethyl acetate. This mixture is washed with water and brine, dried over sodium sulfate, and concentrated. The diastereomers are isolated by silica gel flash chromatography (100% ethyl acetate).

N-((R/S)-Methylphenylphosphinyl)-N-benzyl-D-leucine: A flask containing N-(R/S-methylphenylphosphinyl)-N-benzyl-D-leucine benzylyl ester (2.04 g, 4.53 mmol) and 10% Pd/C (500 mg) is evacuated followed by the addition of methanol. A hydrogen atmosphere is introduced and the reaction is allowed to stir for 45 minutes. The mixture is filtered through celite and the filtrate is collected and concentrated to give N-(R/S-methylphenyl phosphinyl)-N-benzyl-D-leucine as a white glassy substance.

N-Benzyloxy-2(R)-[[(R)-methylphenylphosphinyl] benzylamino]-4-methylpenta-namide and N-benzyloxy-2 (R)-[[(S)-methylphenylphosphinyl]benzylamino]-4-methyl-pentanamide: N-(R/S-Methylphenylphosphinyl)-N-benzyl-D-leucine (1.5 g, 4.17 mmol) is dissolved in N-dimethylformamide and cooled to 0° C. To this is added sequentially hydroxybenzotriazole hydrate (1.69 g, 12.5 mmol), N-methylmorpholine (1.37 mL, 12.5 mmol), and 1-ethyl-3-(3-dimethylaminopropyl) carbodiimide (EDAC, 959 mg, 5 mmol)). After stirring 10 minutes, O-benzylhydroxylamine hydrochloride (666 mg, 4.17 mmol) is added and the reaction is allowed to stir for 3 hours, warming to room temperature. Two diastereomers are observed by TLC. To the mixture is added water, and the mixture is extracted with ethyl acetate. The organics are combined, washed with water and brine, dried over sodium sulfate, and concentrated to give an oil. The diastereomers are then isolated by silica gel flash chromatography (1:1 hexane:ethyl acetate) to give N-benzyloxy-2(R)-[[(R)-methylphenylphosphinyl]benzylamino]-4-methylpentanamide: $R_f$=0.25 (1:1 hexane:ethyl acetate; 31P NMR ($CD_3OD$) d 43.89; and N-benzyloxy-2(R)-[[(S)-methylphenylphosphinyl]benzylamino]-4-methylpentanamide $R_f$=0.15 (1:1 hexane:ethyl acetate).

N-Hydroxy-2(R)-[[(S)-methylphenylphosphinyl]
benzylamino]-4-methylpentanamide: N-Benzyloxy-2(R)-
[[(S)-methylphenylphosphinyl]benzylamino]-4-
methylpentanamide (334 mg, 0.719 mmol) and 80 mg 10%
Pd/C were evacuated in a flask. To this is added 10 mL
methanol and a hydrogen atmosphere is introduced. The
reaction is allowed to stir at room temperature for 2 hours at
which time the reaction appears complete by TLC. The
mixture is filtered through celite; the filtrate is collected and
evaporated to give a white glassy solid. The product is
dissolved in ethyl acetate and hexane is added dropwise until
the product begins to precipitate to give N-hydroxy-2(R)-
[[(R)-methylphenylphosphinyl]benzylamino]-4-
methylpentanamide as colorless solid: MS-IS: m/z 375
[M+H]$^+$, 397 [M+Na]$^+$, 413 [M+K]$^+$.

N-Hydroxy-2(R)-[[(R)-methylphenylphosphinyl]
benzylamino]-4-methylpentanamide: N-Benzyloxy-2(R)-
[[(S)-methylphenylphosphinyl]benzylamino]-4-
methylpentanamide (460 mg, 0.99 mmol) and 10% Pd/C
(100 mg) are evacuated in a flask. To this is added methanol
(10 mL) and a hydrogen atmosphere is introduced. The
reaction is allowed to stir at room temperature for 2 hours at
which time the reaction appears complete by TLC. The
mixture is filtered through celite; the filtrate is collected and
evaporated to give a white glassy solid. The hydroxamic
acid is crystallized by dissolving in ethyl acetate and adding
hexane dropwise until the solution becomes cloudy.
N-Hydroxy-2(R)-[[(R)-methylphenyl-phosphinyl]
benzylamino]-4-methylpentanamide is obtained as a white
crystalline solid: MS-IS m/z 375 [M+H]$^+$, 397 [M+Na]$^+$,
413 [M+K]$^+$. ($R_2$=isobutyl, $R_1$=benzyl, $R_3$=methyl,
$R_4$=phenyl).

EXAMPLE 4

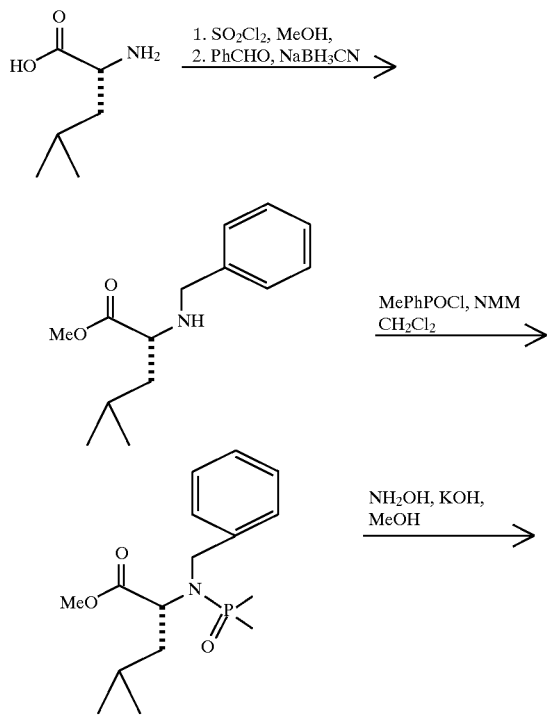

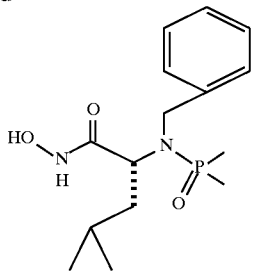

D-Leucine methyl ester hydrochloride: D-leucine (43.63
g, 333 mmol) is dissolved in methanol (400 mL) and cooled
to 0° C. To this is added dropwise thionyl chloride (25.5 mL,
350 mmol). The reaction is allowed to stir 16 hours at room
temperature at which time the volatiles are removed to give
an off-white solid. The product is recrystallized from ethyl
acetate/methanol to give D-leucine methyl ester hydrochloride as a fluffy white solid.

N-Benzyl D-leucine methyl ester: D-Leucine methyl ester
hydrochloride (35 g, 193 mmol) is dissolved in methanol. To
this is added sodium acetate (39.4 g, 480 mmol), followed
by benzaldehyde (19.8 mL, 195 mmol). This mixture is
stirred for 15 minutes and a solution of sodium cyanoborohydride (7.1 g, 113 mmol) in methanol (50 mL) is added
over 15 minutes. After 3 hours the reaction is complete. A
10% aqueous solution of sodium bicarbonate is added with
stirring and after 10 minutes the volatiles are removed. The
product is extracted with ether and washed with water (2×).
The ether mixture is dried over sodium sulfate and evaporated to give 39.9 g of N-benzyl D-leucine methyl ester as
a colorless oil.

N-(Dimethylphosphinyl)-N-benzyl-D-leucine methyl
ester: Dimethylphosphonic chloride (200 mg, 1.78 mmol) is
dissolved in dichloromethane (5 mL) and cooled to 0° C. To
this is added a solution of N-benzyl D-leucine methyl ester
(412 mg, 1.75 mmol), and N-methyl morpholine (0.44 mL,
4 mmol) in dichloromethane (5 mL). A catalytic amount of
4-dimethylaminopyridine is added and the reaction is
allowed to stir 16 hours at room temperature. At this time,
the solids are filtered off, the filtrate collected and evaporated. The crude product is purified by silica gel flash
chromatography (96:4 ethyl acetate:methanol) to give
N-(dimethylphosphinyl)-N-benzyl-D-leucine methyl ester
as a colorless solid.

N-Hydroxy-2(R)-[[dimethylphosphinyl]benzylamino]-
4methylpentanamide: N-(Dimethylphosphinyl)-N-benzyl-
D-leucine methyl ester (158 mg, 0.51 mmol) is treated with
a solution of NH$_2$OK (2.8 mL, 1.76M in methanol) prepared
as described in Fieser and Fieser, Vol. 1, p. 478). The
reaction is allowed to stir 3 hours at room temperature at
which time is determined complete by TLC. The reaction
mixture is neutralized with 1M aqueous HCl; the volatiles
are removed until the product oils out. Methanol is then
added followed by water dropwise until the solution appears
cloudy. The crystals are collected by filtration to give
N-hydroxy-2(R)-[[dimethylphosphinyl]benzylamino]-4-
methyl-pentanamide as a colorless solid: MS-IS m/z 313
[M+H]$^+$, 335 [M+Na]$^+$, 357 [M+K]$^+$. ($R_2$=isobutyl,
$R_1$=benzyl, $R_3$=methyl, $R_4$=phenyl).

EXAMPLE 5

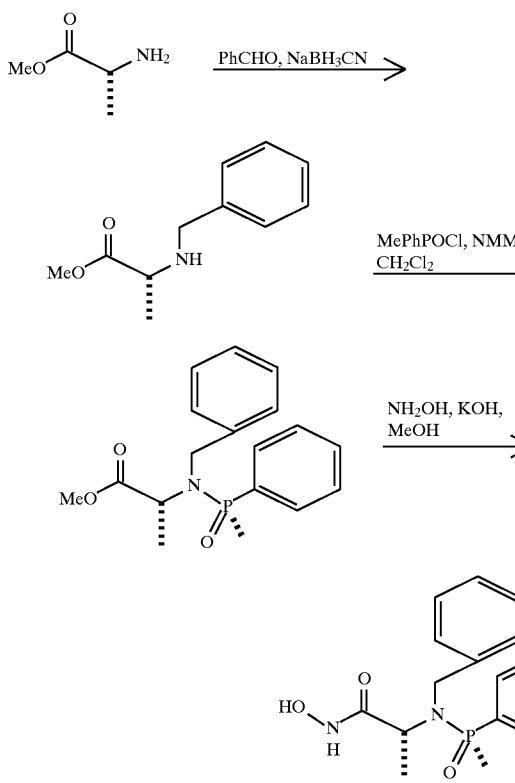

N-Benzyl D-alanine methyl ester: D-Alanine methyl ester (4 g, 28.66 mmol) is taken up in methanol (100 mL). To this is added sodium acetate (5.88 g, 71.65 mmol) and benzaldehyde (2.9 mL, 28.66 mmol). The mixture is stirred for 15 minutes and then a solution of sodium cyanoborohydride (1.08 g, 17.2 mmol) in methanol (5 mL) is added dropwise to the mixture. After stirring for 2 hours methanol is evaporated under reduced pressure and the product is extracted into ether and washed with water (2x). The crude product is purified by silica gel flash chromatography (8:2 hexane:ethyl acetate) to give 3.3 g of N-benzyl D-alanine methyl ester as an oil.

N-((R)-Methylphenylphosphinyl)-N-benzyl-D-alanine methyl ester: Methylphenyl-phosphinic chloride (361 mg, 2.07 mmol) is dissolved in dichloromethane (2.5 mL) and then cooled to 0° C. To this is added a solution of N-benzyl D-alanine methyl ester (400 mg, 2.07 mmol) and N-methyl morpholine (0.51 mL, 4.6 mmol) in dichloromethane (2.5 mL). A catalytic amount of 4-dimethylaminopyridine is then added to the stirring mixture. The reaction is stirred for 16 hours at room temperature, washed with water and brine, dried over sodium sulfate, and concentrated. The crude product is purified by silica gel flash chromatography (100% ethyl acetate) to give N-((R)-methylphenylphosphinyl)-N-benzyl-D-leucine methyl ester as an oil.

N-Hydroxy-2(R)-[[(R)-methylphenylphosphinyl] benzylamino]-propionamide: N-((R)-Methylphenylphosphinyl)-N-benzyl-D-leucine methyl ester (181 mg, 0.55 mmol) is treated with a solution of NH₂OK (2.2 mL, 1.76M in methanol) prepared as described in Fieser and Fieser, Vol. 1, p. 478). The reaction is stirred for 16 hours at which time TLC indicates completion. The reaction mixture is neutralized with 1M aqueous HCl and the volatiles are removed. The desired product is purified over flash silica eluting with THF. The resulting residue is crystallized by dissolving in ethyl acetate and adding hexane until the solution becomes cloudy. N-Hydroxy-2(R)-[[(R)-methylphenylphosphinyl]-benzylamino]-propionamide is obtained as hard, dense colorless crystals: MS-IS m/z 333 [M+H]⁺, 355 [M+Na]⁺. ($R_1$=benzyl, $R_2$=methyl, $R_3$=phenyl, $R_4$=phenyl).

EXAMPLE 6

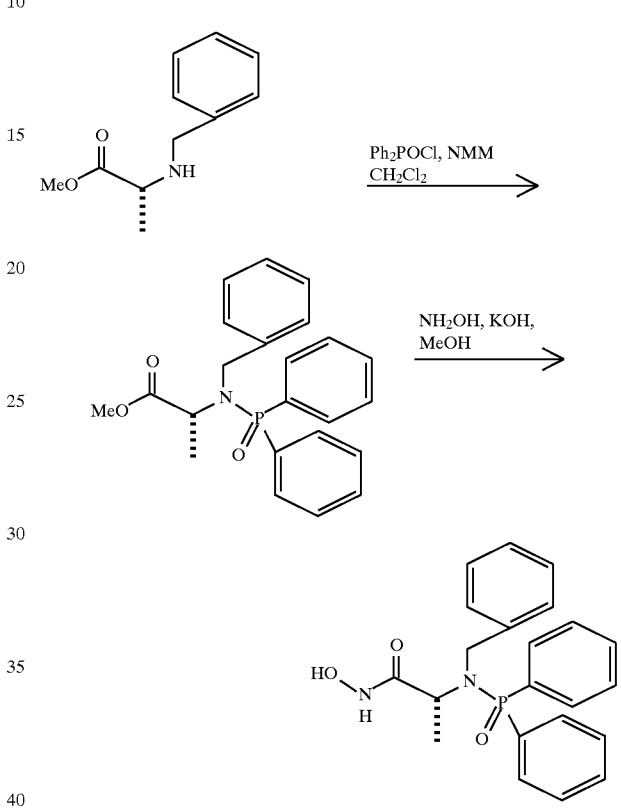

N-(Diphenylphosphinyl)-N-benzyl-D-alanine methyl ester: Diphenylphosphinic chloride (0.2 mL) is dissolved in dichloromethane (5 mL) and cooled to 0° C. To this is added a solution of N-benzyl D-alanine methyl ester (243 mg, 1.26 mmol) and triethylamine (0.39 mL, 2.8 mmol) in dichloromethane (2.5 mL). A catalytic amount of 4-dimethylaminopyridine is added to the reaction. The reaction stirs 48 hours at room temperature. The dichloromethane solution is diluted with 20 mL more dichloromethane and then washed with 1M aqueous HCl (2x). The product is purified by silica gel flash chromatography (8:2 ethyl acetate:hexane) to give N-(diphenylphosphinyl)-N-benzyl-D-alanine methyl ester as an oil.

N-Hydroxy-2R-[[diphenylphosphinyl]benzylamino]-propionamide: To N-(diphenylphosphinyl)-N-benzyl-D-alanine methyl ester (100 mg, 0.25 mmol) is added a solution of NH₂OK (0.88 mL, 1.76M in methanol) prepared as described in Fieser and Fieser, Vol. 1, p. 478. The reaction is stirred for 16 hours at which time TLC indicates completion. The reaction mixture is neutralized with 1M aqueous HCl and the volatiles are removed. The product is purified by silica gel flash chromatography (100% ethyl acetate) to give N-hydroxy-2(R)-[[diphenylphosphinyl]benzylamino]-propionamide as an oil: MS-IS m/z 395 [M+H]⁺, 417 [M+Na]⁺. ($R_1$=benzyl, $R_2$=methyl, $R_3$=phenyl, $R_4$=phenyl).

EXAMPLE 7

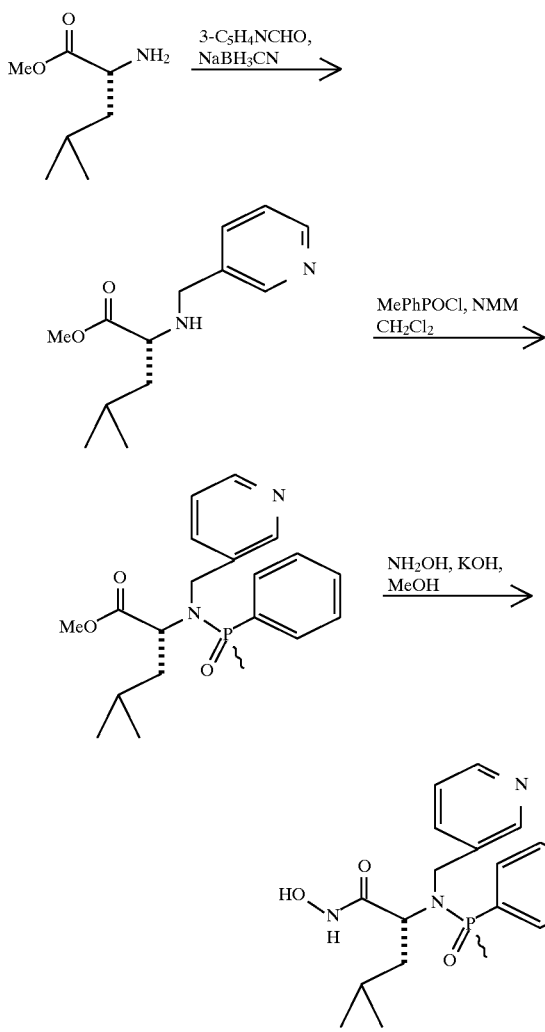

N-(3-Picolyl) D-leucine methyl ester: D-Leucine methyl ester hydrochloride (20 g, 110.43 mmol) is dissolved in methanol. To this is added sodium acetate (22.64 g, 276 mmol) followed by 3-pyridine carboxaldehyde (10.9 mL, 115.5 mmol). The mixture is allowed to stir at room temperature for 15 minutes and then sodium cyanoborohydride (4.15 g, 66 mmol) is added slowly over 15 minutes. After stirring for 16 hours at room temperature methanol is evaporated under reduced pressure and the resulting oil is taken up in ethyl acetate and washed with water (2×). The organics are dried over sodium sulfate and concentrated to an oil. The product is purified by silica gel flash chromatography (100% ethyl acetate) to give N-(3-picolyl) D-leucine methyl ester as an oil.

N-Hydroxy-2(R)-[[(R/S)-methylphenylphosphinyl]3-picolylamino]-4-methytpentan-amide: Methylphenylphosphinic chloride (12.23 g, 70 mmol) is taken up in dichloromethane (100 mL) and cooled to 0° C. To this is added a solution of N-(3-picolyl) D-leucine methyl ester (15.5 g, 65.6 mmol) and N-methyl morpholine (19.24 mL, 175 mmol) in dichloromethane (100 mL). A catalytic amount of 4-dimethylaminopyridine is added and the reaction stirs for 16 hours at room temperature. More methylphenylphosphinic chloride is added (2 g, 11.46 mmol). The reaction continues to stir for 24 hours until complete. By TLC, the diastereomers do not separate. The product is purified by silica gel flash chromatography (5:95 ethanol:ethyl acetate) to give N-((R/S)-methylphenyl-phosphinyl)-N-(3-picolyl) D-leucine methyl ester as an oil. To this ester is added a solution of $NH_2OK$ (250 mL, 1.76M in methanol) prepared as described in Fieser and Fieser, Vol. 1, p. 478. The reaction is stirred for 16 hours at which time TLC indicates completion. The reaction mixture is neutralized with 1M aqueous HCl and the volatiles are removed. The product is purified by silica gel flash chromatography (10:90 ethanol:ethyl acetate) to give 8.6 g of N-hydroxy-2(R)-[[(R/S)-methylphenylphosphinyl]3-picolylamino]-4-methylpentanamide as a 60 (R)/40 (S) mixture of diastereomers: MS-IS m/z 376 [M+H]$^+$, 398[M+Na]$^+$. ($R_1$=3-pyridyl methyl, $R_2$=isobutyl, $R_3$=methyl, $R_4$=phenyl).

EXAMPLE 8

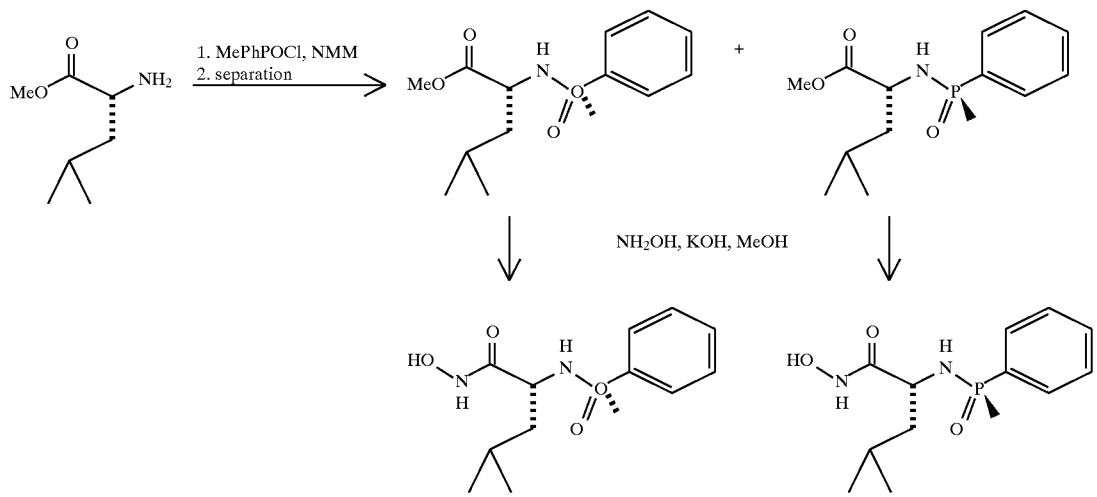

N-((R and S)-Methylphenylphosphinyl)-D-leucine methyl ester: Methylphenyl-phosphinic chloride (113 mg, 0.65 mmol) is dissolved in dichloromethane (5 mL) and then cooled to 0° C. To this is added a solution of D-leucine methyl ester hydrochloride (100 mg, 0.55 mmol) and N-methyl morpholine (0.18 mL, 1.65 mmol) in dichloromethane (3 mL). After stirring 16 hours at room N-hydroxy-2(R)-[[(S)-methylphenylphosphinyl]amino]-4-methylpentanamide as a colorless solid: MS-IS m/z 285 [M+H]+.(R₁=H, R₂=isobutyl, R₃=methyl, R₄=phenyl).

EXAMPLE 9

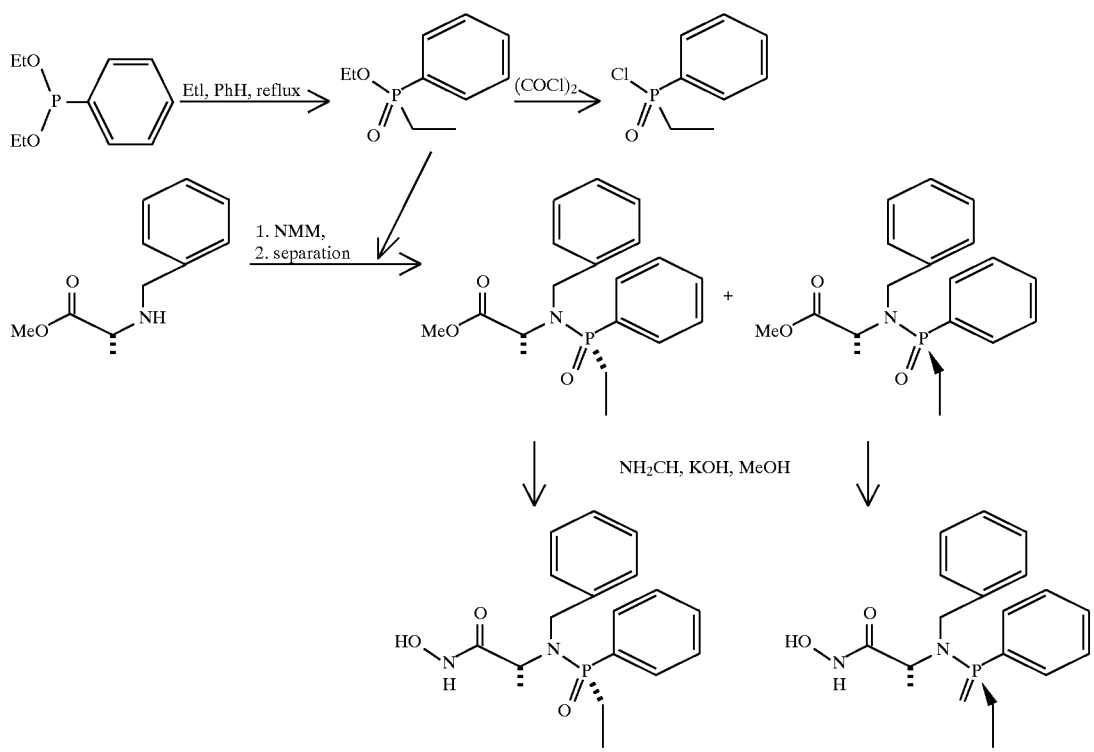

temperature, two spots are observed on tlc. These compounds are separated by silica gel flash chromatography (95:5 ethyl acetate:methanol) to give two diastereomeric products: N-((R)-methylphenylphosphinyl)-D-leucine methyl ester, R_f 0.25 (100% ethyl acetate) and N-((S)-methylphenylphosphinyl)-D-leucine methyl ester, R_f 0.14 (100% ethyl acetate).

N-Hydroxy-2(R)-[[(R)-methylphenylphosphinyl]-4-methylpentanamide: N-((R)-Methylphenylphosphinyl)-D-leucine methyl ester (60 mg, 0.21 mmol) is treated with a solution of NH₂OK (0.57 mL, 1.76M in methanol) prepared as described in Fieser and Fieser, Vol. 1, p. 478. The reaction is stirred for 7 hours at which time TLC indicates completion. The reaction mixture is neutralized with 1M aqueous HCl and the volatiles are removed. The residue is purified by silica gel flash chromatography (95:5 ethyl acetate:ethanol) to give N-hydroxy-2(R)-[[(R)-methylphenylphosphinyl]amino]-4-methylpentanamide as a colorless solid: MS-IS m/z 285 [M+H]+.

N-Hydroxy-2)-[[(S)-methylphenylphosphinyl]amino]-4-methylpentanamide: N-((S)-Methylphenylphosphinyl)-D-leucine methyl ester (55 mg, 0.19 mmol) is treated with a solution of NH₂OK (0.57 mL, 1.76M in methanol) prepared as described in Fieser and Fieser, Vol. 1, p. 478. The reaction is stirred for 6 hours at which time TLC indicates completion. The reaction mixture is neutralized with 1M aqueous HCl and the volatiles are removed. The residue is purified by silica gel flash chromatography (80:20 ethyl acetate:ethanol) followed by crystallization from ethyl acetate/hexane to give Ethyl ethylphenylphosphinate: A mixture of diethyl phenyl phosphonite (4.5 g, 22.70 mmol), ethyl iodide (0.24 mL, 3 mmol) and benzene (100 mL) is stirred and heated at 85° C. for 24 hours. The reaction is 30% complete as indicated by tlc. Another portion of ethyl iodide (0.30 mL, 3.75 mmol) is added and the reaction is stirred for additional 36 hours at 85° C. when it appears complete by tlc. The volatiles are removed on a rotary evaporater to give ethyl ethylphenylphosphinate as an oil.

Ethylphenylphosphinic chloride: To a solution of ethyl ethylphenylphosphinate (2 g, 10 mmol) in benzene (200 mL) is added oxalyl chloride (1.3 mL, 15 mmol). The mixture is stirred for 3 hours at room temperature. The volatiles are removed on a rotary evaporater and the product is dried under vacuum for 12 hours to give ethylphenylphosphinic chloride as an oil.

N-((R and S)-Ethylphenylphosphinyl)-N-benzyl-D-alanine methyl ester: To a solution of ethylphenylphosphinic chloride (1.04 g, 5.5 mmol) in dichloromethane (15 mL) is added a solution of N-benzyl D-alanine methyl ester (1.37 g, 7.1 mmol) and N-methylmorpholine (1.36 mL, 12.4 mmol) in dichloromethane (15 mL). A catalytic amount of 4-dimethylaminopyridine is added and the reaction is stirred 90 hours at room temperature. Two spots are observed on tlc. These compounds are separated by silica gel flash chromatography (95:5 ethyl acetate: methanol) to give two diastereomeric products: N-((S)-ethylphenylphosphinyl)-N-benzyl-D-alanine methyl ester, R_f 0.25 (100% ethyl acetate) and N-((R)-ethylphenylphosphinyl)-N-benzyl-D-alanine methyl ester, R_f 0.35 (100% ethyl acetate).

N-Hydroxy-2(R)-[[(S)-ethylphenylphosphinyl]amino]-propionamide: N-((S)-Ethylphenylphosphinyl)-N-benzyl-D-alanine methyl ester (105 mg, 0.30 mmol) is treated with a solution of $NH_2OK$ (1.0 mL, 1.76M in methanol) prepared as described in Fieser and Fieser, Vol. 1, p. 478. The reaction is stirred for 16 hours at which time TLC indicates completion. The reaction mixture is neutralized with 1M aqueous HCl and the volatiles are removed. The residue is purified by silica gel flash chromatography (95:5 ethyl acetate:methanol) to give N-hydroxy-2(R)-[[(S)-ethylphenylphosphinyl]amino]-propionamide as colorless solid: MS-IS m/z 347 $[M+H]^+$, 369 $[M+Na]^+$.

N-Hydroxy-2(R)-[[(R)-ethylphenylphosphinyl]amino]-propionamide: N-((R)-Ethylphenylphosphinyl)-N-benzyl-D-alanine methyl ester (333 mg, 0.96 mmol) is treated with a solution of $NH_2OK$ (3.3 mL, 1.76M in methanol) prepared as described in Fieser and Fieser, Vol. 1, p. 478. The reaction is stirred for 16 hours at which time TLC indicates completion. The reaction mixture is neutralized with 1M aqueous HCl and the volatiles are removed. The residue is purified by silica gel flash chromatography (95:5 ethyl acetate:methanol) to give 110 mg (33%) of N-hydroxy-2(R)-[[(R)-ethylphenyl-phosphinyl]amino]-propionamide as colorless solid: MS-IS m/z 347 $[M+H]^+$, 369 $[M+Na]^+$. ($R_1$=benzyl, $R_2$=methyl, $R_3$=ethyl, $R_4$=phenyl).

EXAMPLE 10

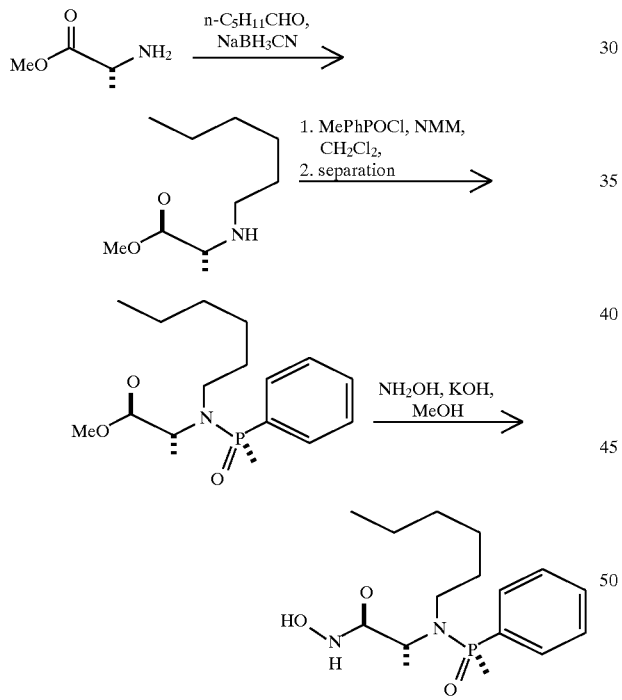

N-Hexyl-D-alanine methyl ester: D-alanine methyl ester (1.5 g, 10.75 mmol) is taken up in 50 mL methanol and is cooled to 0° C. To this is added hexanal (1.3 mL, 10.75 mmol) followed by sodium acetate (2.62 g, 32 mmol). After stirring for 15 minutes at 0° C. sodium cyanoborohydride (440 mg, 7 mmol) is added and the mixture is stirred for further 16 hours at room temperature. The methanol is evaporated and the resulting residue is taken up in ether and is transferred to a separatory funnel, washed with water (2×), dried over sodium sulfate, and is evaporated to give 1.81 g of N-hexyl-D-alanine methyl ester as a colorless oil.

N-((R)-Methylphenylphosphinyl)-N-hexyl-D-alanine methyl ester: Methylphenyl-phosphinic chloride (1.05 g, 6 mmol) is dissolved in dichloromethane (50 mL) and cooled to 0° C. To this is added a solution of N-hexyl-D-alanine methyl ester (1 g, 5.34 mmol) and triethylamine (2.1 mL, 15 mmol) in dichloromethane (10 mL). A catalytic amount of 4-dimethylaminopyridine is added and reaction is stirred for 16 hours, washed with water and brine, dried over sodium sulfate, and concentrated. The crude product is purified by silica gel flash chromatography (100% ethyl acetate) to give N-((R)-methylphenylphosphinyl)-N-hexyl-D-alanine methyl ester as an oil.

N-Hydroxy-2)-[[(R)-methylphenylphosphinyl]hexylamino]-propionamide: N-(R)-Methylphenylphosphinyl)-N-hexyl-D-alanine methyl ester (198 mg, 0.61 mmol) is treated with a solution of $NH_2OK$ (2 mL, 1.76M in methanol) prepared as described in Fieser and Fieser, Vol. 1, p. 478. The reaction is stirred for 16 hours at which time TLC indicates completion. The reaction mixture is neutralized with 1M aqueous HCl and the volatiles are removed. The crude product is purified by preparative TLC (95:5 ethyl acetate:methanol) to give 110 mg of N-hydroxy-2(R)-[[(R)-methylphenylphosphinyl]hexylamino]-propionamide as a colorless solid: MS-IS m/z 327 $[M+H]^+$, 349 $[M+Na]^+$. ($R_1$=2-hexyl, $R_2$=methyl, $R_3$=methyl, $R_4$=phenyl).

Additional examples of compounds of the invention which are made using the methods described above and suitable known starting materials or starting materials made by known methods:

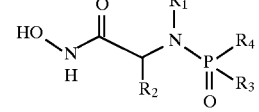

|  | $R_1$ | $R_2$ | $R_3$ | $R_4$ |
| --- | --- | --- | --- | --- |
| Example 11 | $(CH_2)_3$ | $(CH_2)_3$ | ethyl | 4-methoxyphenyl |
| Example 12 | $(CH_2)_4$ | $(CH_2)_4$ | ethyl | 4-nitrophenyl |
| Example 13 | benzyl | (2-methylthio) ethyl | methyl | 2-thienyl |
| Example 14 | propyl | 2-propyl | methoxy | 2-furyl |
| Example 15 | isopropyl | 2-butyl | methyl | 2-pyridyl |
| Example 16 | methoxy methyl | benzyl | methyl | 3-pridyl |
| Example 17 | hydroxy methyl | (3-indole)methyl | methyl | 4-pyridyl |

-continued

|  | R₁ | R₂ | R₃ | R₄ |
|---|---|---|---|---|
| Example 18 | H | (4-hydroxy phenyl)methyl | methyl | 2-fluorophenyl |
| Example 19 | phenyl | 4-aminobutyl | methyl | 4-fluorophenyl |
| Example 20 | ethyl | (4-imidazolyl) methyl | methyl | 2-methoxyphenyl |
| Example 21 | butyl | aminocyl methyl | methyl | 4-methoxy 2-pyridyl |
| Example 22 | methyl | amino methyl ethyl | methyl | ethyl |
| Example 23 | benzyl | benzyl | methyl | phenyl |
| Example 24 | methyl | methyl | methyleneoxy | |
| Example 25 | 4-methoxy benzyl | isobutyl | methyl | phenyl |
| Example 26 | benzyl | isopropyl | methyl | methyl |
| Example 27 | phenylethyl | methyl | methyl | phenyl |
| Example 28 | cyclohexylmethyl | methyl | methyl | 4-methoxyphenyl |
| Example 29 | 3-pyridylmethyl | benzyl | methyl | phenyl |

These examples provide the skilled artisan with sufficient guidance as to making the present invention and do not limit it in any way.

Composition and Method of Use Examples

The compounds of the invention are useful to prepare compositions for the treatment of ailments and the like. The following composition and method examples do not limit the invention, but provide guidance to the skilled artisan to prepare and use the compounds, compositions and methods of the invention. In each case the compounds formula I may be substituted for the example compound shown below with similar results.

The methods of use exemplified do not limit the invention, but provide guidance to the skilled artisan to use the compounds, compositions and methods of the invention. The skilled practitioner will appreciate that the examples provide guidance and may be varied based on condition and the patient.

Example A

A tablet composition for oral administration, according to the present invention, is made comprising:

| Component | Amount |
|---|---|
| Example 9 | 15. mg |
| Lactose | 120. mg |
| Maize Starch | 70. mg |
| Talc | 4. mg |
| Magnesium Stearate | 1. mg |

Other compounds having a structure according to Formula (I) are used with substantially similar results.

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
|---|---|
| Example 3 | 15% |
| Polyethylene glycol | 85% |

Other compounds having a structure according to Formula (I) are used with substantially similar results.

A human male subject weighing 90 kg (198 lbs), suffering from osteoarthritis, is treated by a method of this invention. Specifically, for 5 years, a capsule containing 70 mg of Example 3 is administered daily to said subject.

At the end of the treatment period, the patient is examined via orthoscopy, and found to have no further advancement of erosion/fibrillation of the articular cartilage.

Example C

A saline-based composition for local administration, according to the present invention, is made comprising:

| Component | Amount (% w/w) |
|---|---|
| Example 13 | 5% |
| Polyvinyl alcohol | 15% |
| Saline | 80% |

Other compounds having a structure according to Formula (I) are used with substantially similar results.

A patient having deep corneal abrasion applies the drop to each eye twice a day. Healing is speeded, with no visual sequelae.

Example D

An topical composition for local administration, according to the present invention, is made comprising:

| Component | Composition (% w/v) |
|---|---|
| Compound of Example 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s |
| Total = | 100.00 |
| Total = | 100.00 |

Any of the other compounds having a structure according to Formula (I) are used with substantially similar results.

A patient suffering from chemical burns applies the composition at each dressing change (b.i.d.). Scarring is substantially diminished.

Example E

A inhalation aerosol composition, according to the present invention, is made comprising:

| Component | Composition (% w/v) |
|---|---|
| Compound of Example 2 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Any of the other compounds having a structure according to Formula (I) are used with substantially similar results.

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 5 | 0.10 |
| Benzalkonium chloride | 0.01 |
| EDTA | 0.05 |
| Hydroxyethylcellulose (NATROSOLM %) | 0.50 |
| Sodium metabisulfite | 0.10 |
| Sodium chloride (0.9%) | q.s |
| Total = | 100.0 |

Any of the other compounds having a structure according to Formula (I) are used with substantially similar results.

A human male subject weighing 90 kg (198 lbs), suffering from corneal ulcerations, is treated by a method of this invention. Specifically, for 2 months, a saline solution containing 10 mg of Example 5 is administered to said subjects affected eye twice-daily.

Example G

A composition for parenteral administration is made comprising:

| Component | Amount |
|---|---|
| Example 4 | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Other compounds having a structure according to Formula I are used with substantially similar results.

Example H

A mouthwash composition is prepared;

| Component | % w/v |
|---|---|
| Example 1 | 3.00 |
| SDA 40 Alcohol | 8.00 |
| Flavor | 0.08 |
| Emulsifier | 0.08 |
| Sodium Fluoride | 0.05 |
| Glycerin 10.00 | |
| Sweetener | 0.02 |
| Benzoic acid | 0.05 |
| Sodium hydroxide | 0.20 |
| Dye | 0.04 |
| Water | balance to 100% |

A patient with gum disease uses 1 ml of the mouthwash thrice daily to prevent further oral degeneration.

Other compounds having a structure according to Formula I are used with substantially similar results.

Example I

A lozenge composition is prepared;

| Component | % w/v |
|---|---|
| Example 3 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the losenge to prevent loosening of an implant in the maxilla. Other compounds having a structure according to Formula I are used with substantially similar results.

Example J
Chewing Gum Composition

| Component | w/v % |
|---|---|
| Example 1 | 0.03 |
| Sorbitol crystals | 38.44 |
| Paloja-T gum base* | 20.00 |
| Sorbitol (70% aqueous solution) | 22.00 |
| Mannitol | 10.00 |
| Glycerine | 7.56 |
| Flavor | 1.00 |

A patient chews the gum to prevent loosening to prevent loosening of dentures.

Other compounds having a structure according to Formula I are used with substantially similar results.

Example K

| Component | w/v % |
| --- | --- |
| USP Water | 54.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

Example 1 is prepared by first mixing 80 kg of gylcerin and all of the benzyl alcohol and heating to 65 C., then slowly adding and mixing together methylparaben, propylparaben, water, xanthan gum, and guar gum. Mix these ingredients for about 12 minutes with a Silverson in-line mixer. Then slowly add in the following ingredients in the following order: remaining glycerin, sorbitol, antifoam C, calcium carbonate, citric acid, and sucrose. Separately combine flavors and coolants and then slowly add to the other ingredients. Mix for about 40 minutes.

The patient takes the formulation to prevent flare up of colitis.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula I,

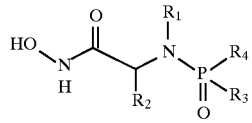

wherein:
$R_1$ is hydrogen, alkyl, alkynylalkyl, alkenylalkyl, arylalkyl, heterocycle-alkyl, alkoxy-alkyl, arylalkoxy-alkyl, or alkylthioalkyl;

$R_2$ is hydrogen, alkyl, alkynyl, alkenyl, aryl-alkyl, heterocycle-alkyl, heteroalkyl (including alkoxy-alkyl, arylalkoxy-alkyl, or alkylthioalkyl alkylaminoalkyl, arylthioalkyl, arylalkylthioalkyl), heterocyclylheteroalkyl, aminoacylalkyl, acylaminoalkyl, alkoxycarbonylalkyl, acyloxyalkyl;

$R_1$ and $R_2$ together form an alkylene chain or heteroalkylene chain;

$R_3$ is alkyl, cycloalkyl, cycloheteroalkyl, carbocyclic or heterocyclic aryl, heteroalkyl (hydroxyalkyl, alkoxyalkyl, or aminoalkyl); and $R_3$ and $R_2$ may together form an alkylene chain or hetero alkylene chain;

$R_4$ is alkyl, alkoxy, arylalkyl, cycloalkyl, carbocyclic or heterocyclic aryl;

an optical isomer, diastereomer or enantiomer thereof, or a pharmaceutically-acceptable salt, or biohydrolyzable alkoxyamide, ester acyloxyamide, or imide thereof.

2. A compound having a structure according to claim 1,

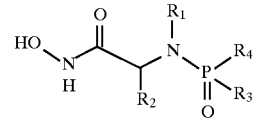

wherein:
$R_1$ is hydrogen alkyl, aryl-alkyl, heterocycle-alkyl, alkoxy-alkyl, arylalkoxy-alkyl, or alkylthioalkyl;

$R_2$ is hydrogen, alkyl, aryl-alkyl, heterocycle-alkyl, alkoxy-alkyl, arylalkoxy-alkyl, alkylthioalkyl or alkylthio;

$R_3$ is alkyl, cycloalkyl, carbocyclic or heterocyclic aryl, hydroxyalkyl, alkoxyalkyl, or aminoalkyl; and $R_4$ is carbocyclic or heterocyclic aryl;

a stereoisomer thereof or enantiomer thereof, or a pharmaceutically-acceptable salt, or biohydrolyzable alkoxyamide, ester acyloxyamide, or imide thereof.

3. The compound of claim 2, wherein $R_1$ is chosen from H, arylalkyl, alkyl and heterocycle alkyl.

4. The compound according to claim 2 wherein $R_2$ is H or $C_1$–$C_6$alkyl.

5. The compound of claim 2, wherein $R_4$ is phenyl or substituted phenyl.

6. The compound of claim 5, wherein $R_4$ is substituted phenyl and the substitution is with alkoxy.

7. The compound of claim 6, wherein the $R_4$ is substituted with methoxy, and butoxy.

8. The compound of claim 2, wherein $R_3$ is $C_1$–$C_6$ lower alkyl or phenyl.

9. The compound of claim 8, wherein $R_2$ is H, isobutyl or methyl.

10. The compound according to claim 9, wherein $R_1$ is chosen from n-phenyl, phenylethyl, benzyl, pyridyl methyl, or methyl.

11. The compound of claim 1, wherein the compound is selected from;

N-Hydroxy-2-[[diphenylphosphinyl](2-phenylethyl)-amino]-acetamide;

N-Hydroxy-2-[[methylphenylphosphinyl](2-phenylethyl)-amino]-acetamide;

N-Hydroxy-2(R)-[[(R)-methylphenylphosphinyl]benzylamino]-4-methylpentanamide;

N-Hydroxy-2(R)-[[dimethylphosphinyl]benzylamino]-4-methylpentanamide;

N-Hydroxy-2(R)-[[(R)-methylphenylphosphinyl]benzyl-amino]-propionamide;

N-Hydroxy-2(R)-[[diphenylphosphinyl]benzylamino]-propionamide;

N-Hydroxy-2(R)-[[(R/S)-methylphenylphosphinyl]3-picolyl-amino]-4-methylpentanamide;

N-Hydroxy-2(R)-[[(S)-methylphenylphosphinyl]amino]-4-methylpentanamide;

N-Hydroxy-2(R)-[[(R)-ethylphenyl-phosphinyl]amino]-propionamide; or

N-Hydroxy-2(R)-[[(R)-methylphenyl-phosphinyl]hexylamino]-propionamide.

12. A pharmaceutical composition comprising:

(a) a safe and effective amount of a compound of claim 1; and
(b) a pharmaceutically-acceptable carrier.

13. A pharmaceutical composition comprising:
(a) a safe and effective amount of a compound of claim 3; and
(b) a pharmaceutically-acceptable carrier.

14. A pharmaceutical composition comprising:
(a) a safe and effective amount of a compound of claim 6; and
(b) a pharmaceutically-acceptable carrier.

15. A pharmaceutical composition comprising:
(a) a safe and effective amount of a compound of claim 7; and
(b) a pharmaceutically-acceptable carrier.

16. A pharmaceutical composition comprising:
(a) a safe and effective amount of a compound of claim 10; and
(b) a pharmaceutically-acceptable carrier.

17. A method for preventing or treating a disease associated with unwanted metalloprotease activity in a mammalian subject, the method comprising administering to said subject a safe and effective amount of a compound of claim 1.

18. A method for preventing or treating a disease associated with unwanted metalloprotease activity in a mammalian subject, the method comprising administering to said subject a safe and effective amount of a compound of claim 3.

19. A method for preventing or treating a disease associated with unwanted metalloprotease activity in a human or other animal subject, the method comprising administering to said subject a safe and effective amount of a compound of claim 6.

20. A method for preventing or treating a disease associated with unwanted metalloprotease activity in a mammalian subject, the method comprising administering to said subject a safe and effective amount of a compound of claim 10.

21. A method for preventing or treating a disorder modulated by metalloproteases, wherein the disorder is chosen from the group comprising, arthritis, cancer, cardiovascular disorders, skin disorders ocular disorders, inflammation and gum disease by administering to a mammal in need of such treatment, a safe and effective amount of a metalloprotease inhibitor according to claim 1.

22. A method for preventing or treating a disorder according to claim 21, wherein the disorder is arthritis, and is chosen from the group comprising, osteoarthritis and rheumatoid arthritis.

23. A method for preventing or treating a disorder according to claim 21, wherein the disorder is cancer, and the treatment prevents or arrests tumor growth and metastasis.

24. A method for the preventing or treating a disorder according to claim 21, wherein the disorder is a cardiovascular disorder chosen from the group comprising dilated cardiomyopathy, congestive heart failure, atherosclerosis, plaque rupture, reperfusion injury, ischemia, chronic obstructive pulmonary disease, angioplasty restenosis and aortic aneurysm.

25. A method for the preventing or treating a disorder according to claim 21, wherein the disorder is an ocular disorder, and is chosen from the group comprising, corneal ulceration, lack of corneal healing, macular degeneration, and pterygium.

26. A method for preventing or treating a disorder according to claim 21, wherein the disorder is gum disease, and is chosen from the group comprising, periodontal disease, and gingivitis.

27. A method for preventing or treating a condition, according to claim 21, wherein the condition is skin condition chosen from the group comprising wrinkle repair and prevention, U.V. skin damage, epidermolysis bullosa, psoriasis, sclerodema, atopic dermatitis and scarring.

28. A method for preventing the loosening of prosthetic devices chosen from the group comprising joint replacements and dental prosthesis by administering to a mammal in need of such treatment, a safe and effective amount of a metalloprotease inhibitor according to claim 1.

29. A method for treating inflammatory conditions according to claim 21, chosen from the group comprising inflammatory bowel disease, Crohn's Disease, ulcerative colitis, pancreatitis, diverticulitis, acne inflammation, osteomylitis, bronchitis, arthritis, asthma.

30. A method of treating multiple sclerosis, comprising administering to a mammal in need of such treatment, a safe and effective amount of a metalloprotease inhibitor according to claim 1.

31. A method for treating musculoskeletal disease or cachexia comprising administering to a mammal in need of such treatment, a safe and effective amount of a metalloprotease inhibitor according to claim 1.

* * * * *